(12) United States Patent
Choi et al.

(10) Patent No.: US 9,951,336 B2
(45) Date of Patent: Apr. 24, 2018

(54) COMPOSITION FOR REDUCING SENESCENCE OF CELL OR SUBJECT COMPRISING SMURF2 INHIBITOR AND USE THEREOF

(71) Applicant: Samsung Electronics Co., Ltd., Suwon-si, Gyeonggi-do (KR)

(72) Inventors: Kobong Choi, Osan-si (KR); Joontae Park, Seoul (KR); Hyuntae Kang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/925,746

(22) Filed: Oct. 28, 2015

(65) Prior Publication Data

US 2016/0186181 A1 Jun. 30, 2016

(30) Foreign Application Priority Data

Dec. 26, 2014 (KR) .................. 10-2014-0191129

(51) Int. Cl.
| | | |
|---|---|---|
| *C12N 15/11* | (2006.01) | |
| *C12N 15/113* | (2010.01) | |
| *A61K 45/06* | (2006.01) | |
| *A61K 31/713* | (2006.01) | |

(52) U.S. Cl.
CPC ........ *C12N 15/1137* (2013.01); *A61K 31/713* (2013.01); *A61K 45/06* (2013.01); *C12Y 603/02* (2013.01); *C12N 2310/11* (2013.01); *C12N 2310/14* (2013.01); *C12N 2320/30* (2013.01)

(58) Field of Classification Search
CPC .............................. C12N 15/1137; A61K 45/06
See application file for complete search history.

(56) References Cited

U.S. PATENT DOCUMENTS

| | | | |
|---|---|---|---|
| 6,506,559 B1 * | 1/2003 | Fire .................... | A61K 31/7105 435/325 |
| 7,354,722 B1 | 4/2008 | Thomsen et al. | |
| 2010/0183514 A1 | 7/2010 | Glimcher et al. | |
| 2013/0122046 A1 | 5/2013 | Li et al. | |

FOREIGN PATENT DOCUMENTS

| | | |
|---|---|---|
| WO | WO 00/77168 A2 * | 12/2000 |
| WO | WO 2004-070002 A2 | 8/2004 |

OTHER PUBLICATIONS

Zhang et al. Genes & Development 18:3028-3040, 2004.*
Kaneki et al. The Journal of Biological Chemistry vol. 281, 4326-4333, 2006.*
ASBMR 2011 presenting author, Sabine Guth-Gundel, Annual Meeting Smurf inhibition does not increase bone mass, Sep. 19, 2011, p. 1.*
Mack Nature Biotechnology 25, 631-648, Table 1, MicroRNA gets down to business, 1 page.*
Saiednia et al. Curr Drug Discov Technol. 2015;12(4):218-24.*
Boccardi et al. Ageing Research Reviews 22 (2015) 1-8.*
Ramkumar et al., "Smurf2 Regulates the Senescence Response and Suppresses Tumorigenesis in Mice", *Cancer Research*, 72(11): 2714-2719 (2012).
Ramkumar et al., "Smurf2 regulates hematopoietic stem cell self-renewal and aging", *Aging Cell* 13: 478-486 (2014).

* cited by examiner

*Primary Examiner* — Brian A Whiteman
(74) *Attorney, Agent, or Firm* — Leydig, Voit & Mayer, Ltd.

(57) ABSTRACT

A composition for reducing a level of senescence of a cell or subject, a method of reducing a level of senescence in a cell or subject by using the composition, and a method of preventing and treating symptoms or diseases related to or caused by senescence of a cell or subject.

9 Claims, 8 Drawing Sheets scramble siRNA smurf2 siRNA

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic smurf2 siRNA

<400> SEQUENCE: 1
guuaaugacu ggaagguaa                                                    19

<210> SEQ ID NO 2
<211> LENGTH: 19
<212> TYPE: DNA
<213> ORGANISM: Artificial Sequence
<220> FEATURE:
<223> OTHER INFORMATION: Synthetic scramble siRNA

<400> SEQUENCE: 2
auacaguggu agaguauga                                                    19
```

COMPOSITION FOR REDUCING SENESCENCE OF CELL OR SUBJECT COMPRISING SMURF2 INHIBITOR AND USE THEREOF

RELATED APPLICATION

This application claims the benefit of Korean Patent Application No. 10-2014-0191129, filed on Dec. 26, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: One 676 Byte ASCII (Text) file named "720971_ST25.TXT" created Oct. 6, 2015.

BACKGROUND

1. Field

The present disclosure relates to a composition for reducing a level of senescence of a cell or a subject, a method of reducing a level of senescence in a cell or a subject by using the composition, and a method of preventing and treating symptoms or diseases related to or caused by senescence of a cell or a subject.

2. Description of the Related Art

Senescence or aging is a degenerative phenomenon that occurs over time. In the case of humans, physiological activities may deteriorate with aging and the activities of certain enzymes or the secretion of certain hormones may increase. Senescence is a permanent halt of cellular division. Replicative senescence or cellular senescence has been observed as an aging model at the cell level. When cells are continuously cultured, cells divide multiple times, but cells can no longer divide as they get older. Senescent cells are resistant against programmed cell death, and some senescent cells remain in a non-dividing state for several years.

SMAD specific E3 ubiquitin protein ligase 2 ("Smurf2") is one type of E3 ubiquitin protein ligase. It is known that Smurf2 binds to SMADs, which play a key role in the regulation of the TGF-beta signaling pathway, and thereby regulates the stability of TGF-beta proteins.

There remains a need for a composition and a method of reducing senescence by regulating the expression of the activity of Smurf 2 in a cell or a subject.

SUMMARY

Provided is a method of reducing a level of senescence of a cell, the method comprising administering an inhibitor of the expression or the activity of Smurf2 to a senescent cell or a subject comprising the cell.

Provided is a method of preventing and treating a symptom or disease caused by cellular senescence, the method comprising administering an inhibitor of the expression or the activity of Smurf2 to a senescent cell or a subject comprising the cell.

Related methods and compositions also are provided.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
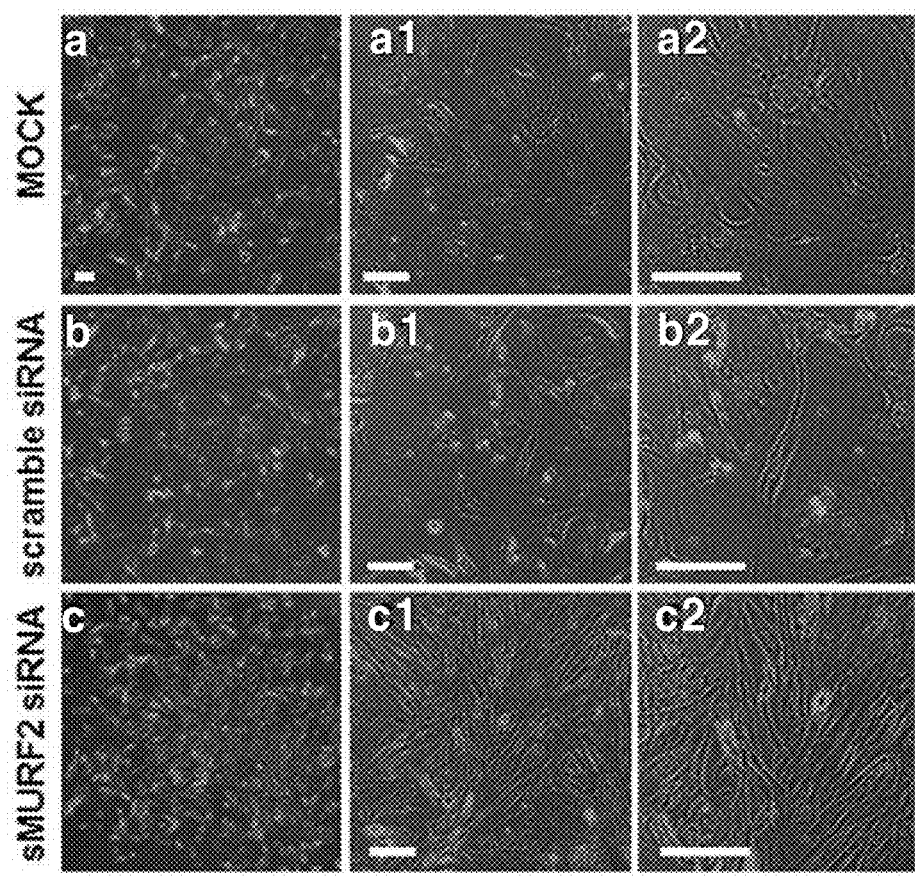
FIG. 1 is a series of images displaying senescent cells wherein "Mock" indicates a negative control, "scramble siRNA" indicates a senescent cell transfected with a scramble siRNA, and "smurf2 siRNA" indicates a senescent cell transfected with a smurf2 siRNA.

Provided is a composition useful for reducing a level of senescence of a cell, wherein the composition includes an inhibitor of the expression or activity of Smurf2. Senescence refers to an array of changes which occur over time in a cell or a subject. When compared to a reference cell (i.e., a non-senescent cell of the same type), a senescent cell is defined as a cell that exhibits at least one selected from a decrease in the proliferation of one or more cell types, an increase of an accumulation of lipofuscin, an increase of an activity of β-galactosidase, an increase of mitochondrial-derived reactive oxygen species, and an increase of a mitochondrial membrane potential (MMP). When compared to a reference cell (i.e., a senescent cell of the same type), a young cell is defined as a cell that exhibits at least one selected from an increase in the proliferation of one or more cell types, a decrease of accumulation of lipofuscin, a decrease of activity of β-galactosidase, a decrease of mitochondrial-derived reactive oxygen species, and a increase of a MMP. For example, a cell having a doubling time that is twice or more, three times or more, four times or more, five times or more, six times or more, seven times or more, nine times or more, ten times or more, fifty times or more, or a hundred times or more than that of a reference cell that has been passaged (i.e., subcultured) twice may be a senescent cell. In the case of a human, a cell that is taken from a person about 30 years old or older, about 40 years old or older, about years old or older, about 60 years old or older, about 70 years old or older, about 80 years old or older, about 90 years old or older, about 100 years old or older may be a senescent cell. Senescence of a subject, as used to herein, refers to senescence in a cell or tissue of a subject, Smurf2 is one type of E3 ubiquitin protein ligase. Smurf2 is bound to SMADs, which play a key role in the regulation of TGF-beta signaling pathway, and thereby regulate the stability of TGF-beta protein. Smurf2 may be, for example, a protein encoded by a nucleotide sequence of GenBank Accession No. NM_022739 or a protein including an amino acid sequence of GenBank Accession No. NP_073576 in a human. Smurf2 may be, for example, a protein encoded by a nucleotide sequence of GenBank Accession No.

NM_025481 or a protein including an amino acid sequence of GenBank Accession No. NP_079757 in a mouse. Smurf2 may be a protein consisting of 748 amino acids. The Smurf2 may be a protein including a C2 domain, a WW1 domain, a WW2 domain, a WW3 domain, a HECT domain, or a combination thereof.

The inhibitor of expression of Smurf2 may be an agent that suppresses protein synthesis. For example, the inhibitor of expression may be a small interfering RNA (siRNA), a microRNA (miRNA), an antisense oligonucleotide, or a combination thereof. An siRNA is an RNA molecule involved in RNA interference that interferes with the expression of one or more genes, thereby suppressing the production of one or more specific proteins. A length of the siRNA may be in a range of about 10 nucleotides (hereinafter 'nt') to about 50 nt, about 15 nt to about 40 nt, about 20 nt to about 30 nt, or about 21 nt to about 23 nt. The inhibitor of expression of Smurf2 may be a siRNA that includes the nucleotide sequence of SEQ ID NO: 1 or a fragment thereof. The fragment may be a polynucleotide having about two or more consecutive nucleotides of SEQ ID NO: 1. The length of the fragment of SEQ ID NO: 1 may be, for example, in a range of about 2 nt to about 18 nt, about 3 nt to about 18 nt, about 4 nt to about 17 nt, about 5 nt to about 16 nt, about 6 nt to about 15 nt, or about 7 nt to about 10 nt. A miRNA is a small RNA that plays a role in regulation of gene expression in an organism, and a length of a miRNA may be in a range of about 17 nt to about 25 nt. A miRNA binds to a complementary sequence in a mRNA so as to increase or decrease a production of one or more specific proteins. An antisense oligonucleotide is a single strand DNA or a RNA that is complementary to a specific sequence, and thus, bind to a complementary sequence in a mRNA so as to increase or decrease a production of one or more specific proteins.

The inhibitor of activity of Smurf2 may be an agent that suppresses protein function. The inhibitor of activity of Smurf2 may be a compound, a nucleic acid, an ion, an antibody, an anti-peptide, or a combination thereof.

The cell, for example, may be a nerve cell, an immune cell, an epithelial cell, a reproductive cell, a muscle cell, or a cancer cell. The cell may be a fibroblast or an early senescent cell. The early senescent cell may be from a progeria cell.

The subject, for example, may be a human, cattle, a horse, a pig, a dog, sheep, a goat, a rat, a mouse, a rabbit, or a cat.

Reducing of the level of senescence of a cell or a subject may involve delaying senescence of the cell or subject, preventing the cell or subject from senescence, or transforming a senescent cell or subject into a young cell or subject (e.g., reverting a senescent cell or a subject having a senescent cell to a state that is similar to that of a pre-senescent cell or a subject having one or more pre-senescent cells). For example, the reducing of the level of senescence of a cell or subject may include at least one selected from increasing a proliferation ability of the cell, increasing phosphorylation of Unc-51 like autophagy activating kinase 1 (ULK1), decreasing an activity of β-galactosidase, increasing autophagy, decreasing an accumulation of lipofuscin, decreasing mitochondrial-derived reactive oxygen species, and increasing a mitochondrial membrane potential (MMP). The increasing of a proliferation ability of a cell may be a decrease of a cell doubling time or an increase in cellular division times. The β-galactosidase may be a β-galactosidase related to senescence.

The composition may be useful for preventing or treating a symptom or disease related to or caused by senescence of a cell or subject. The symptom or disease related to or caused by senescence of a cell or subject may be a skin wrinkle, slow scar regeneration, a degenerative brain disease (for example, Alzheimer's disease, Parkinson's disease, and dementia), a stroke, diabetes (for example, a type 2 diabetes), arthritis, artery hardening, a heart disease, alopecia, osteoporosis, sarcopenia, progeria, lysosome storage disease, or a combination thereof. The symptom or disease related to or caused by senescence of a cell or subject may be a disease related to or caused by accumulation of lipofuscin. Lipofuscin is a yellow-brown autofluorescent pigment granule in cells. Lipofuscin is used as a senescence index and is referred to as an aging pigment. Accumulation of lipofuscin may be found on the retina, liver, kidney, or heart of an old person or patient who suffer from a wasting disease for a long time lipofuscin. The disease associated to accumulation of lipofuscin may be neuronal ceroid lipofuscinoses (NCL), macular degeneration, neurofibrillary tangles, Brown atrophy of the heart, Alzheimer's disease, Parkinson's disease, amyotrophic lateral sclerosis (ALS), acromegaly, denervation atrophy, lipid myopathy, chronic obstructive pulmonary disease (COPD), Melanosis Coli, Atherosclerosis, or a combination thereof.

The term "preventing" as used herein refers to suppression or the delay of an onset of a symptom or disease related to or caused by senescence by the administration of a composition. The term "treating" as used herein refers to the improvement or advantageous change of a symptom or disease related to or caused by senescence by administering a composition.

The composition may be a pharmaceutical composition. The composition may further include a pharmaceutically acceptable carrier. With regard to the composition, a "pharmaceutically acceptable carrier" refers to a material that is used in combination with an active ingredient to help an application of the active ingredient, generally an inert material. The carrier may include a conventional pharmaceutically acceptable excipient, additive, or diluent. The carrier, for example, may include at least one selected from a filler, a binder, a disintegrant, a buffer, a preservative, an antioxidant, a lubricating agent, a flavoring agent, a thickener, a coloring agent, an emulsifier, a suspending agent, a stabilizer, and an isotonizing agent.

The composition may include an inhibitor of expression or activity of Smurf2 or a pharmaceutically acceptable salt or solvate thereof at a "therapeutically effective amount". With regard to the composition, a "therapeutically effective amount" refers to a sufficient amount which is therapeutically effective upon being administered to a subject in a need of treatment. The effective amount may be determined according to factors including severity of disease, patient's age, weight, health conditions, sex, sensitivity to drug, drug administration time, administration route, discharge rate, treatment period, and drugs which are mixed or used in combination with the composition of the exemplary embodiment, and other factors which are well known in the medical field. The "effective amount" may be present in the composition in a range of about 0.01 mg to about 10,000 mg, about 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg.

The composition, for example, may be administered in a dose of about 0.001 mg/kg to about 100 mg/kg for adults once a day, several times a day, or once every several days.

The composition may be administered orally, or parenterally. The parenteral administration may include an intravenous administration, an intraperitoneal administration, a subcutaneous administration, a rectal administration, and a topical administration. Accordingly, the composition may be formulated in a variety of forms, such as a tablet, a capsule, an aqueous solution, or a suspension. An excipient, such as lactose or corn starch and a lubricating agent, such as magnesium stearate may be commonly added to a parenteral tablet. In the case of parenteral capsule, lactose and/or dried corn starch may be used as a diluent. In case there is a need of an aqueous suspension for the parenteral administration, active ingredients may be combined with an emulsifier and/or a suspension. If needed, a certain sweetening agent and/or a flavoring agent may be added thereto. In the case of the intraneural administration, the intramuscular administration, the intraperitoneal administration, the subcutaneous administration, and the intravenous administration, a sterilized solution of active ingredients are prepared, and pH of thereof needs to be adjusted and buffered appropriately. In the case of the intravenous administration, a concentration of a solute needs to be adjusted to obtain an isotonic formulation. The composition may be an aqueous solution containing a pharmaceutically acceptable carrier such as brine that has a pH of 7.4. The aqueous solution may be administered in intramuscular or intraneural blood flow of a patient via a local bolus injection.

The composition may include at least one medicine for treating a symptom or disease related to or caused by senescence of a cell or a subject.

Provided is a method of reducing a level of senescence of a cell or subject, including administering an inhibitor of the expression or activity of Smurf2 to a cell or subject.

The Smurf2, inhibitor of expression of Smurf2, inhibitor of activity of Smurf2, cell, subject, senescence, and cell or reducing a level of senescence of a cell or subject are the same as described above.

The subject, for example, may be a human, cattle, a horse, a pig, a dog, sheep, a goat, a rat, a mouse, a rabbit, or a cat. The subject may suffer from or at risk for developing a symptom or disease related to or caused by senescence or symptom or disease related to or caused by senescence.

The administration of the Smurf2 inhibitor, for example, may be in a dose of about 0.001 mg/kg to about 100 mg/kg for adults once a day, several times a day, or once every several days during a period of several days to one year. The administration may be carried out using a method that is known to those in the art. The administration, for example, may be carried out by using any method that allows a direct administration to a subject, such as an oral administration, an intravenous administration, an intramuscular administration, a transdermal administration, a mucosal administration, an intranasal administration, an intratracheal administration, or a subcutaneous administration. The administration may be a topical or systemic administration. The administration may be a topical administration of the inhibitor to a tissue including a senescent cell.

Provided is a method of preventing and treating of a symptom or disease related to or caused by senescence of a cell or subject, including administering an inhibitor of expression or activity of Smurf2 to a cell or subject.

The Smurf2, inhibitor of expression of Smurf2, inhibitor of activity of Smurf2, cell, subject, administration, senescence, preventing and treatment of a symptom or disease related to or caused by senescence of a cell or subject or are the same as described above.

The methods described above may further include identifying a senescent cell or a subject having one or more senescent cells by, e.g., measuring the lipofuscin accumulation in the cell or a subject in comparison to a reference cell or a reference subject or determining the cell doubling time of a cell or a specific cell type within a subject in comparison to a reference cell or a reference subject.

When a composition for reducing a level of senescence of a cell or subject, a method of reducing a level of senescence of a cell or subject using the composition, and a method of preventing or treatment of a symptom or disease related to or caused by senescence of a cell or subject according to an exemplary embodiment is administered/practiced, a level of senescence of a cell or subject having one or more senescent cells may effectively be reduced, and a symptom or disease related to or caused by senescence may be well prevented or treated.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Example 1

Proliferation Induction or Recovery of Senescent Cell by Using Smurf2 siRNA (1) Proliferation Induction of Senescent Cell by Using Smurf2 siRNA In order to verify whether a senescent cell proliferates after it has been transfected with a Smurf2 siRNA, a human dermal fibroblast (HDF) M11 cell was taken from an 11-year-old boy. The HDF M11 cell was cultured in medium supplemented with a high concentration of glucose, glutamine, and Dulbecco's Modified Eagle's Medium containing pyruvate (hereinafter referred to as 'DMEM'), 10% (v/v) fetal bovine serum (FBS), and 1× penicillin/streptomycin at about 37° C. and 5% $CO_2$ atmosphere and was subsequently passaged 35 times in order to prepare senescent cells. Cells having a doubling time of at least about 10 days after passaging were considered senescent cells.

Prepared senescent cells were first transfected with a Smurf2 siRNA having a final concentration of about 25 nM or a scramble siRNA having a random sequence by using Lipofectamine® RNAiMAX transfection reagent (available from Life technologies). Once the first transfection was complete, the medium was replaced with fresh medium, and was continued to be cultured at 37° C. and 5% $CO_2$ atmosphere for two days. Nucleotide sequences of the Smurf2 siRNA and scramble siRNA are as follows: smurf2 siRNA: 5'-GUUAAUGACUGGAAGGUAA-3' (SEQ ID NO: 1), scramble siRNA: 5'-AUACAGUGGUAGA-GUAUGA-3' (SEQ ID NO: 2)

Once the first transfection was complete, the prepared senescent cells were transfected in the same manner as in the first transfection, and then were continued to be cultured at 37° C. and 5% $CO_2$ atmosphere for two days. Once the second transfection was complete, the prepared senescent cells were transfected in the same manner as in the first transfection, and then were continued to be cultured at 37° C. and 5% $CO_2$ atmosphere for two weeks. A cell that was not transfected with a Smurf2 siRNA or a scramble siRNA was designated as a negative control.

The cultured cell was observed by a microscope, and the image is shown in FIG. 1. In FIG. 1. "Mock" indicates the negative control, scramble siRNA indicates the senescent cell transfected with a scramble siRNA, and smurf2 siRNA indicates the senescent cell transfected with a Smurf2 siRNA. In addition, a1 to c1 are each an enlarged image of a to c, respectively, and a2 to c2 are each an enlarged image of a1 to c1, respectively. As shown in FIG. 1, the proliferation of the senescent cells transfected with smurf2 siRNA increased compared to that of the senescent cells transfected with scramble siRNA or negative control, and the morphology of the cells were the same as that of young cells. Accordingly, it was found that proliferation of senescent cells was induced by the smurf2 siRNA transfection.

(2) Confirmation of Decrease of Smurf2 Protein Expression and Phosphorylation Induction of Unc-51 Like Autophagy Activating Kinase 1 (ULK1) by Smurf2 siRNA It was verified whether Smurf2 protein expression decreased and phosphorylation of ULK1, which is related to autophagy, increased by performing transfection of a senescent cell with a smurf2 siRNA.

A senescent cell was transfected in the same manner as in Example 1(1). A protein was taken from the transfected senescent cell, and immunoblot was carried out by using an anti-Smurf2 antibody (available from Santa cruz biotechnology, Inc. Cat. No. SC-25511), anti-p-ULK1 antibody (available from Cell Signaling Technology, Cat. No. 5869s), and anti-GAPDH antibody (available from Abm Inc, Cat. No. G041).

Figure 2:
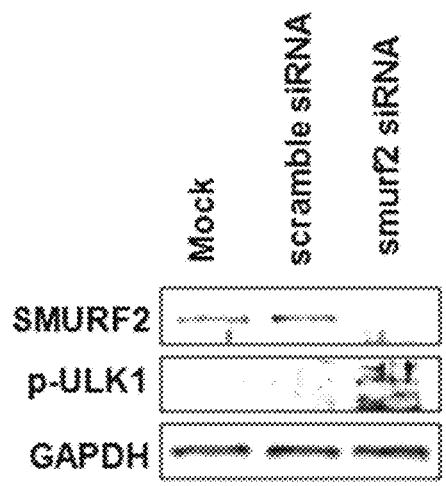
FIG. 2 is an immunoblot analysis of the expression levels of certain proteins by a senescent cell transfected with Smurf2 siRNA, a senescent cell transfected with scramble siRNA, and a negative control ("Mock")

FIG. 2 shows the obtained immunoblot image. As shown in FIG. 2, an amount of proteins of the senescent cell transfected with Smurf2 siRNA decreased, and an amount of phosphorylated ULK1 of the senescent cell transfected with Smurf2 siRNA increased, compared to the senescent cell transfected with scramble siRNA and the negative control. Accordingly, it was found that Smurf2 protein expression decreased, and phosphorylation of ULK1 was induced by the transfection of a senescent cell with Smurf2 siRNA.

(3) Decrease of the Number of Senescent Cells Due to Smurf2 siRNA

A senescent cell may have an increased level of activity of a senescence-associated beta-galactosidase (SA β-gal), and thereby the senescent cell may be stained blue in X-gal staining. It was verified whether the number of senescent cells decreased due to the smurf2 siRNA transfection by examining activity of SA β-gal.

A senescent cell was transfected with a Smurf2 siRNA or scramble siRNA in the same manner as in Example 1(1), except that the senescent cell was cultured for one week during the third transfection. A cell that was not transfected with a Smurf2 siRNA and a scramble siRNA was designated as a negative control.

Figure 3A:
FIG. 3A is a pair of microscopic images of a senescent cell transfected with a smurf2 siRNA or scramble siRNA, respectively, wherein the senescence-associated beta-galactosidase (SA β-gal) expressed by each cell is shown.
Figure 3A:
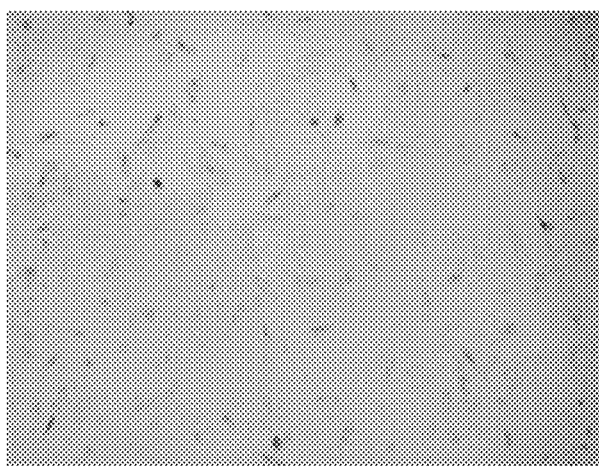

Then, the senescent cell was stained by using a Cellular Senescence Assay Kit (available from Cell Signaling Technology, Cat. No. 9860), and the number of cells stained blue were counted by observing through a microscope. FIG. 3A shows the obtained microscope image. The ratio of the number of stained senescent cells transfected with a Smurf2 siRNA or scramble siRNA to the number of stained cells of the negative control was analyzed, and the results thereof are shown in FIG. 3B.

Figure 3B:
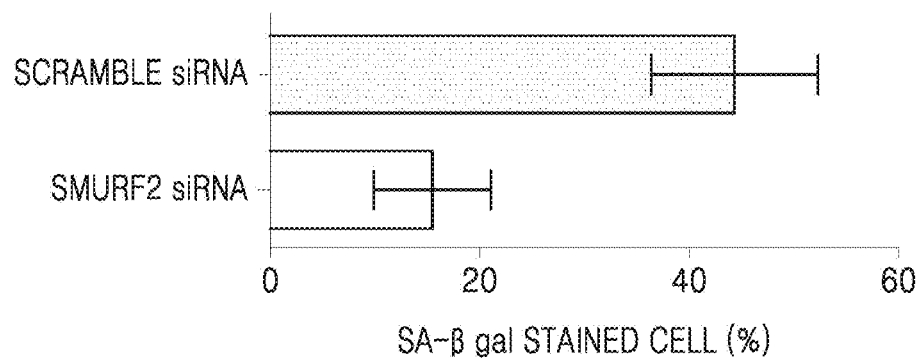
FIG. 3B is a graph showing a ratio of the number of stained senescent cells transfected with a Smurf2 siRNA or scramble siRNA as compared to the number of stained senescent cells of the negative control.

As shown in FIGS. 3A and 3B, about 44% of the senescent cells transfected with the scramble siRNA were stained, as compared to about 16% of the senescent cells transfected with the Smurf2 siRNA. Accordingly, the activity of SA β-gal decreases due to the Smurf2 siRNA transfection, resulting in a decrease of the number of senescent cells.

(4) Recovery of Senescent Cell Due to Smurf2 siRNA

In a senescent cell, autophagy decreases, lipofuscin accumulates, and mitochondria are damaged. It was verified that whether a level of senescence of a senescent cell is recovered due to Smurf2 siRNA transfection.

A senescent cell was transfected with aSmurf2 siRNA or scramble siRNA in the same manner as in Example 1(1). A cell that was not transfected with a Smurf2 siRNA and a scramble siRNA was designated as a negative control.

Figure 4A:
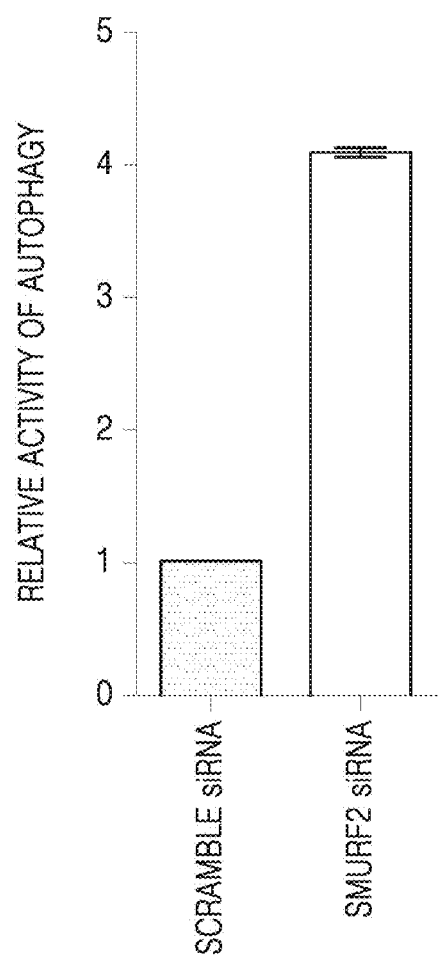
FIGS. 4A to 4D are graphs displaying a ratio of activity of autophagy, lipofuscin autofluorescene, reactive oxygen species (ROS), and mitochondrial membrane potential (MMP), respectively in senescent cells transfected with a Smurf2 siRNA or scramble siRNA.

In order to measure activity of autophagy of the senescent cell, the prepared senescent cell was stained by using a Cyto-ID® Autophagy detection kit (available from ENZO Life Sciences). A relative activity of an autophagy ratio of a senescent cell transfected with a Smurf2 siRNA to a senescent cell transfected with a scramble siRNA was calculated, and the results are shown in FIG. 4A. As shown in FIG. 4A, the senescent cell transfected with a Smurf2 siRNA showed an increase of about 4 times in autophagy compared to the senescent cell transfected with a scramble siRNA. Accordingly, it was found that autophagy is induced in the senescent cell transfected with a Smurf2 siRNA.

Figure 4B:
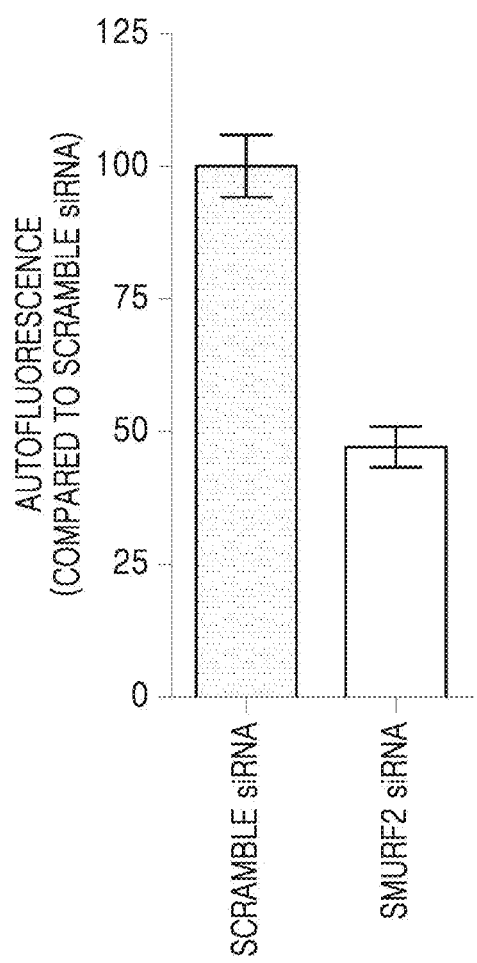

As lipofuscin in a senescent cell emits autofluorescence, accumulation of lipofuscin was analyzed by measuring the fluorescent radiation having a wavelength of 520 nm while irradiating the senescent cell with rays having a wavelength of about 488 nm by using a FACSCaliber (available from Beckton Dickson). The relative autofluorescence ratio of the senescent cell transfected with a Smurf2 siRNA to the senescent cell transfected with a scramble siRNA was calculated, and the results are shown in FIG. 4B. As shown in FIG. 4B, the senescent cell transfected with a Smurf2 siRNA showed about 46% decrease in autofluorescence than the senescent cell transfected with a scramble siRNA. Accordingly, it was found that accumulation of lipofuscin decreases in the senescent cell transfected with a Smurf2 siRNA.

In order to measure a level of mitochondrial function in a senescent cell, the amount of reactive oxygen species (ROS) in the prepared senescent cell was measured by using a MITOSOX™ Red Mitochondrial Superoxide indicator (available from Life technologies). Relative ROS amount ratio of the senescent cell transfected with a Smurf2 siRNA to the senescent cell transfected with a scramble siRNA was analyzed, and the results are shown in FIG. 4C.

In addition, mitochondrial membrane potential (MMP) was measured by using a MitoProbe™ JC-1 Assay kit for Flow Cytometry (available from Life technologies, Cat. No. T3168) in accordance with the manufacturer's instructions. 5,5',6,6'-tetrachloro-1,1',3,3'-tetraethylbenzimidiazolo-carbocyanine iodide (JC-1) accumulates in a mitochondrion dependent upon a transmembrane potential, and this accumulation is indicated by a fluorescence emission shift from green (wavelength of about 529 nm) to red (wavelength of about 590 nm). Mitochondrial depolarization is indicated by a decrease of a ratio of red to green fluorescence intensity. The mitochondrial depolarization was analyzed by flow cytometry using 488 nm excitation and a 530/30 nm and 585/42 nm band-pass filter by using a FACSCaliber (available from Beckton Dickson). The obtained result was analyzed by using a Cell Quest 3.2 software (available from Beckton Dickson). Relative MMP ratio of the senescent cell transfected with a scramble siRNA to the senescent cell transfected with a Smurf2 siRNA was calculated, and the results are shown in FIG. 4D.

Figure 4C:
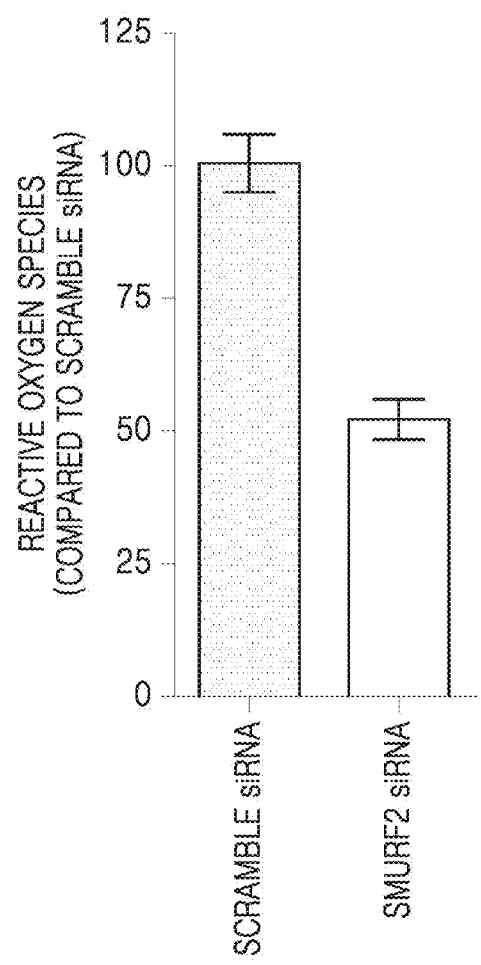
Figure 4D:
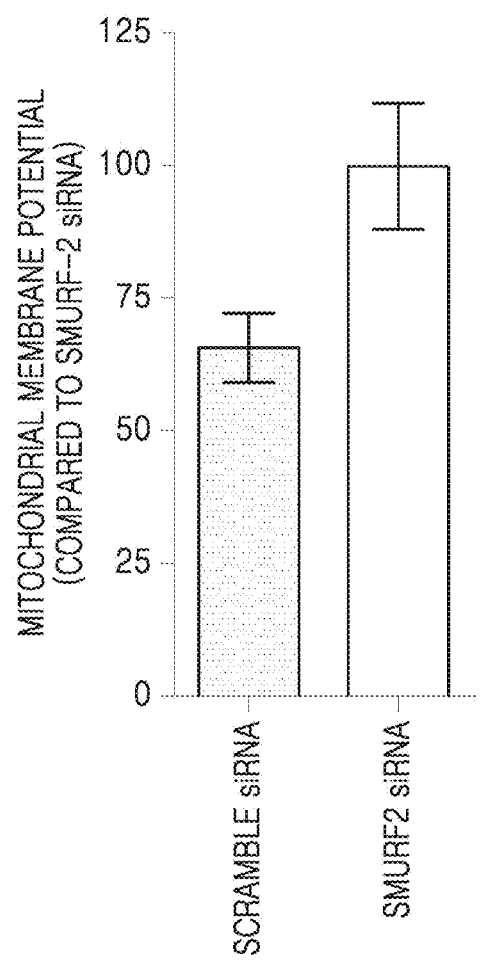

As shown in FIG. 4C, the senescent cell transfected with a Smurf2 siRNA showed about 54% decrease in an amount of ROS than the senescent cell transfected with a scramble siRNA. In addition, as shown in FIG. 4D, the MMP of the senescent cell transfected with a scramble siRNA was about 65% of that of the senescent cell transfected with a Smurf2 siRNA. Accordingly, it was found that mitochondria in the senescent cell are recovered from damage when transfected with a smurf2 siRNA.

Therefore, it was confirmed that Smurf2 siRNA induces activity of autophagy in a senescent cell, reduces accumulation of lipofuscin, and recovers mitochondria damage, thereby reducing a level of senescence in a senescent cell.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reducing senescence of a senescent cell, the method comprising
administering to the senescent cell, in vitro, a small interfering RNA (siRNA) comprising SEQ ID NO: 1 targeting SMAD specific E3 ubiquitin protein ligase 2 (Smurf2) in the senescent cell, thereby increasing a proliferation ability of the cell, increasing phosphorylation of Unc-51 like autophagy activating kinase 1 (ULK1), decreasing an activity of β-galactosidase, increasing autophagy, decreasing an accumulation of lipofuscin, decreasing mitochondrial-derived reactive oxygen species, increasing a mitochondrial membrane potential (MMP), or a combination thereof.

2. The method of claim 1, wherein reducing senescence of a cell comprises delaying senescence of the cell, or transforming a senescent cell into a pre-senescent cell.

3. The method of claim 1, wherein reducing cellular senescence comprises increasing cell proliferation, increasing phosphorylation of Unc-51 like autophagy activating kinase 1 (ULK1), decreasing the activity of β-galactosidase, increasing autophagy, decreasing the accumulation of lipofuscin, decreasing mitochondrial-derived reactive oxygen species, and increasing an MMP.

4. A method of treating a symptom or disease caused by cellular senescence, the method comprising administering to a senescent cell a siRNA comprising SEQ ID NO: 1 targeting Smurf2, whereby a symptom or disease caused by the cellular senescence is treated,
wherein the symptom or disease is a skin wrinkle, slow scar regeneration, macular degeneration, or an accumulation of lipofuscin.

5. The method of claim 4, wherein the symptom or disease caused by cellular senescence is a skin wrinkle or slow scar regeneration.

6. The method of claim 4, wherein the symptom or disease related to or caused by cellular senescence is accumulation of lipofuscin.

7. The method of claim 4, wherein the symptom or disease related to or caused by cellular senescence is macular degeneration.

8. The method of claim 4, wherein the administration is a topical or systemic administration.

9. The method of claim 8, wherein the administration is a topical administration to a tissue comprising a senescent cell.

* * * * *